(12) United States Patent
Farris

(10) Patent No.: US 9,709,828 B2
(45) Date of Patent: Jul. 18, 2017

(54) ATHLETICS VISUAL AID FOCUS DEVICE

(71) Applicant: Jeffrey H. Farris, Hattiesburg, MS (US)

(72) Inventor: Jeffrey H. Farris, Hattiesburg, MS (US)

(*) Notice: Subject to any disclaimer, the term of this patent is extended or adjusted under 35 U.S.C. 154(b) by 35 days.

(21) Appl. No.: 14/748,227

(22) Filed: Jun. 23, 2015

(65) Prior Publication Data

US 2016/0341980 A1 Nov. 24, 2016

Related U.S. Application Data

(62) Division of application No. 13/168,142, filed on Jun. 24, 2011.

(51) Int. Cl.
| | |
|---|---|
| *G02C 7/16* | (2006.01) |
| *G02C 7/10* | (2006.01) |
| *A63B 71/10* | (2006.01) |
| *A63B 59/50* | (2015.01) |
| *A63B 69/00* | (2006.01) |
| *A61F 9/02* | (2006.01) |
| *A63B 102/18* | (2015.01) |

(52) U.S. Cl.
CPC .............. *G02C 7/165* (2013.01); *A63B 59/50* (2015.10); *A63B 71/10* (2013.01); *G02C 7/10* (2013.01); *G02C 7/104* (2013.01); *G02C 7/16* (2013.01); *A61F 9/022* (2013.01); *A63B 2069/0055* (2013.01); *A63B 2102/18* (2015.10); *A63B 2243/0037* (2013.01); *G02C 2200/08* (2013.01)

(58) Field of Classification Search
CPC . G02C 7/165; G02C 7/16; G02C 7/10; G02C 7/104; G02C 2200/08; G02C 9/00; G02C 1/02; A63B 71/10
USPC .................................. 351/41, 44, 45, 46, 47
See application file for complete search history.

(56) References Cited

U.S. PATENT DOCUMENTS

| | | | | |
|---|---|---|---|---|
| 1,637,406 | A | | 7/1922 | Brumder |
| 2,114,658 | A | | 4/1938 | Noffsinger |
| 2,139,275 | A | * | 12/1938 | Lee ........................... G02C 7/16 2/13 |
| 2,358,602 | A | * | 9/1944 | Snyder ................... G02C 7/105 2/12 |
| 3,628,854 | A | * | 12/1971 | Jampolsky ............. G02C 5/001 351/159.58 |
| 3,791,722 | A | * | 2/1974 | Ahlberg ................. G02C 7/105 2/427 |
| 4,824,234 | A | * | 4/1989 | Sparks ..................... G02C 9/00 351/47 |
| 5,177,510 | A | * | 1/1993 | Peters .................... G02C 5/001 351/45 |
| 5,189,445 | A | | 2/1993 | Stagner |
| 5,305,027 | A | * | 4/1994 | Patterson ................ G02C 7/16 351/159.3 |
| 5,355,182 | A | * | 10/1994 | Barbera ................. A61F 9/022 351/159.48 |

(Continued)

*Primary Examiner* — William R Alexander

(57) ABSTRACT

An athletics visual aid focus device is disclosed. The athletics visual aid focus device providing horizontal tunnel vision may be worn by athletes to block out peripheral visual distractions. The athletics visual aid focus device may include upper and lower opaque regions disposed to block out peripheral vision along horizontal planes above and below the user's eyes and may provide a lower transparent region allowing the user to position his feet without head movement.

17 Claims, 2 Drawing Sheets

(56) References Cited

U.S. PATENT DOCUMENTS

| | | | |
|---|---|---|---|
| 5,432,568 A * | 7/1995 | Betz | G02C 7/105 351/45 |
| 5,488,438 A * | 1/1996 | Cochran | A61F 9/02 351/41 |
| 5,552,841 A * | 9/1996 | Gallorini | G02C 7/101 351/44 |
| 5,561,480 A * | 10/1996 | Capes | G02C 5/001 351/45 |
| 5,675,398 A * | 10/1997 | Moore | G02C 7/16 351/45 |
| 5,682,220 A * | 10/1997 | Sherman | G02C 7/16 351/45 |
| 5,956,114 A * | 9/1999 | Tassier | G02C 5/001 351/158 |
| 6,159,397 A * | 12/2000 | Friedman | B29C 45/372 264/1.7 |
| 6,558,266 B2 * | 5/2003 | McMahon | A63B 69/3608 33/262 |
| 6,942,336 B2 | 9/2005 | Foulke | |
| 6,957,889 B1 * | 10/2005 | Steinbock | G02C 7/16 351/45 |
| 7,048,371 B1 | 5/2006 | Moore | |
| D652,857 S * | 1/2012 | Finochiaro | D16/301 |
| 8,998,407 B1 * | 4/2015 | Welt | G02C 7/16 351/45 |
| 2002/0122151 A1 * | 9/2002 | Goldblatt | G02C 7/16 351/46 |
| 2005/0190341 A1 * | 9/2005 | Russomagno | G02C 7/16 351/46 |
| 2006/0072065 A1 | 4/2006 | Fernandez | |
| 2007/0046888 A1 * | 3/2007 | Kurzrok | G02C 7/12 351/45 |
| 2008/0151175 A1 * | 6/2008 | Gross | G02C 7/086 351/45 |
| 2009/0066907 A1 * | 3/2009 | Kopren | A61H 5/00 351/45 |
| 2012/0069291 A1 * | 3/2012 | Singelyn | G02C 7/16 351/47 |
| 2012/0329583 A1 * | 12/2012 | Farris | A63B 71/10 473/422 |
| 2013/0030393 A1 * | 1/2013 | Bogdan | A61F 9/0026 604/302 |

* cited by examiner

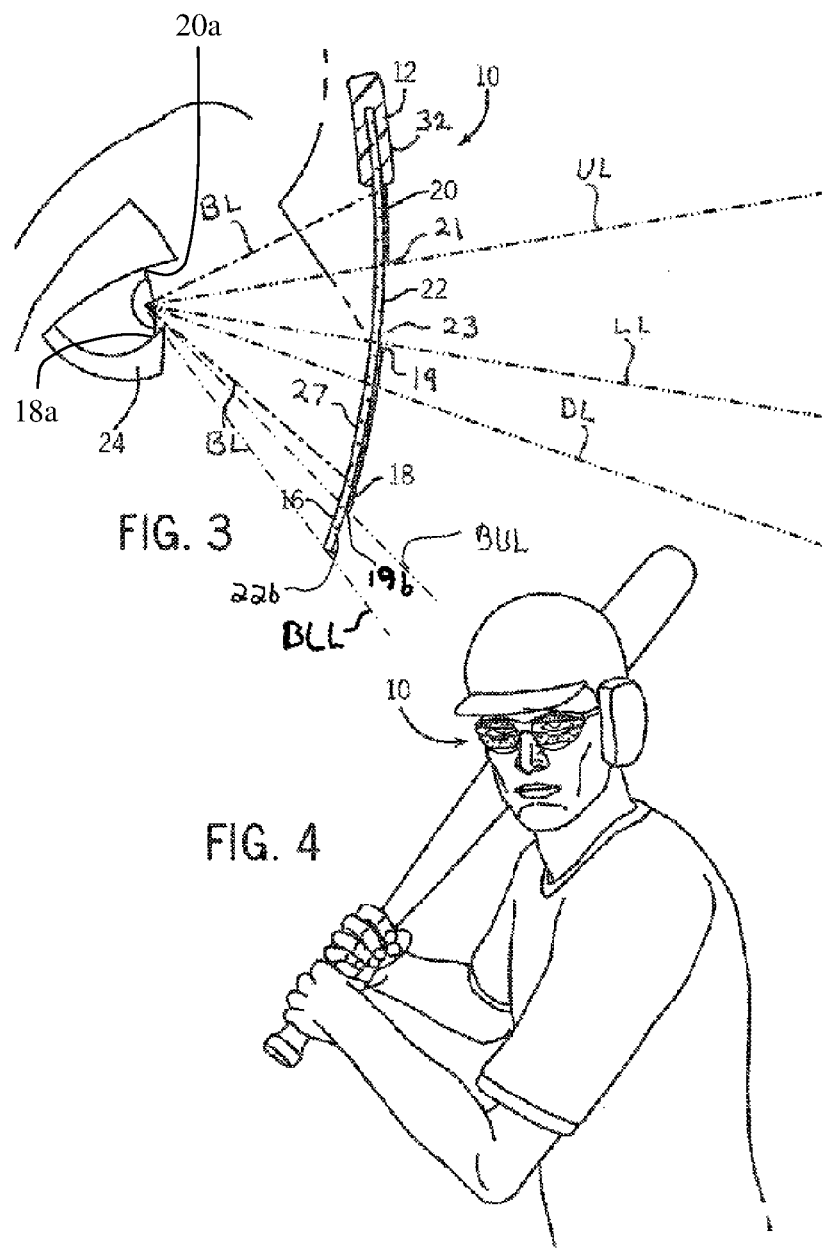

ATHLETICS VISUAL AID FOCUS DEVICE

CROSS-REFERENCE TO RELATED APPLICATIONS

This application is a continuation-in-part application of U.S. patent application Ser. No. 13/168,142 filed Jun. 24, 2011 currently pending and incorporated herein by reference.

FEDERALLY SPONSORED RESEARCH

Not applicable.

BACKGROUND OF THE INVENTION

The present invention generally relates to sports training aids, and more particularly, to a visual aid focus device.

In some sports, an athlete's performance is dependent partially on focus and the ability to concentrate on the action being performed. The better one can maintain focus on a particular action or movement, the higher the likelihood, the athlete will succeed at it. Indeed, some athlete's and coaches preach being able to mentally block out everything but the goal at hand. For example, a baseball or softball player may spend countless hours swinging a round bat trying to hit a moving round ball hurled speeding at them; what some consider the most difficult feat in sports.

One of the obstacles that inhibits an athlete's success in an action is the distractions within a surrounding environment. For example, a common distraction in sports is a surrounding crowd attending the game or match. A crowd sitting in stands may actively attempt to distract an athlete by waving arms, towels, etc. in an attempt to momentarily catch the athlete's eye and distract him from an impending action (for example, hitting a pitch or shooting a basketball). The crowd or even other players may passively also serve as a distraction engaging in routine movement which is picked up by the athlete's field of view (for example, fans walking about, player's moving into position on a baseball diamond). The athlete's brain may subconsciously register this movement thus, distributing focus or concentration away from the task at hand. As can be seen, there is a need for device that can block distractions from the peripheral vision of an athlete.

SUMMARY OF THE INVENTION

In one aspect of the present invention, an athletics visual aid focus device comprises a frame and a lens coupled to the frame. The athletics visual aid focus device also comprises an opaque upper portion of the lens, an opaque lower portion of the lens, and a transparent region juxtaposed between the opaque upper and lower portions of the lens.

In another aspect of the present invention, an athletics visual aid focus device comprises a frame configured to mount in front of a user's eyes, one or more upper baffles coupled to the frame disposed to cover an upper peripheral vision along a horizontal plane above the user's eyes, and one or more lower baffles coupled to the frame disposed to cover a lower peripheral vision along a horizontal plane below the user's eyes, wherein a lower edge of the one or more upper baffles and are disposed spaced from an upper edge of the one or more lower baffles to define a tunnel vision field of view there between.

These and other features, aspects and advantages of the present invention will become better understood with reference to the following drawings, description and claims.

BRIEF DESCRIPTION OF THE DRAWINGS

FIG. 3 is a side view of the athletics visual aid focus device taken along the line 3-3 of FIG. 2 illustrating a tunnel vision created by the device during use; and FIG. 4 is an illustration of an exemplary use of the athletics visual aid focus device as worn by a user.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims. Various inventive features are described below that can each be used independently of one another or in combination with other features.

Broadly, embodiments of the present invention generally provide an athletics visual aid focus device that can be used by, for example, an athlete (also sometimes referred to as a user in the following disclosure). The athletics visual aid focus device may provide a user with an aid to increase focus by providing a tunnel vision to the user thus, enhancing a user's focus on a task at hand.

Figure 1:
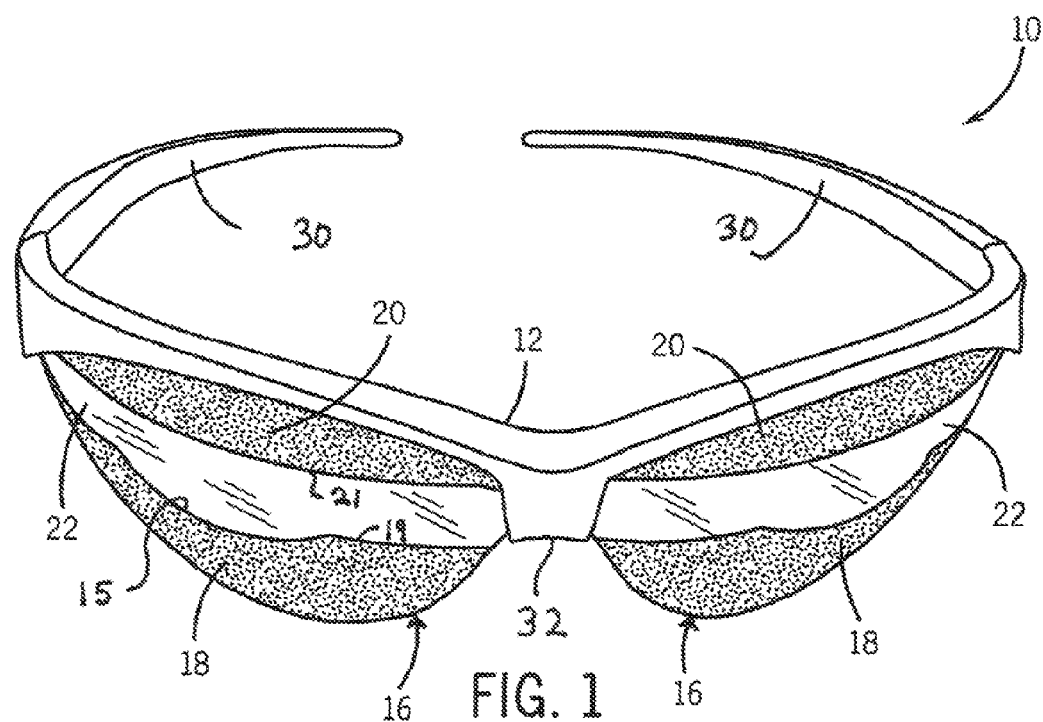
FIG. 1 is a frontal perspective view of an athletics visual aid focus device according to an exemplary embodiment of the present invention.
Figure 2:
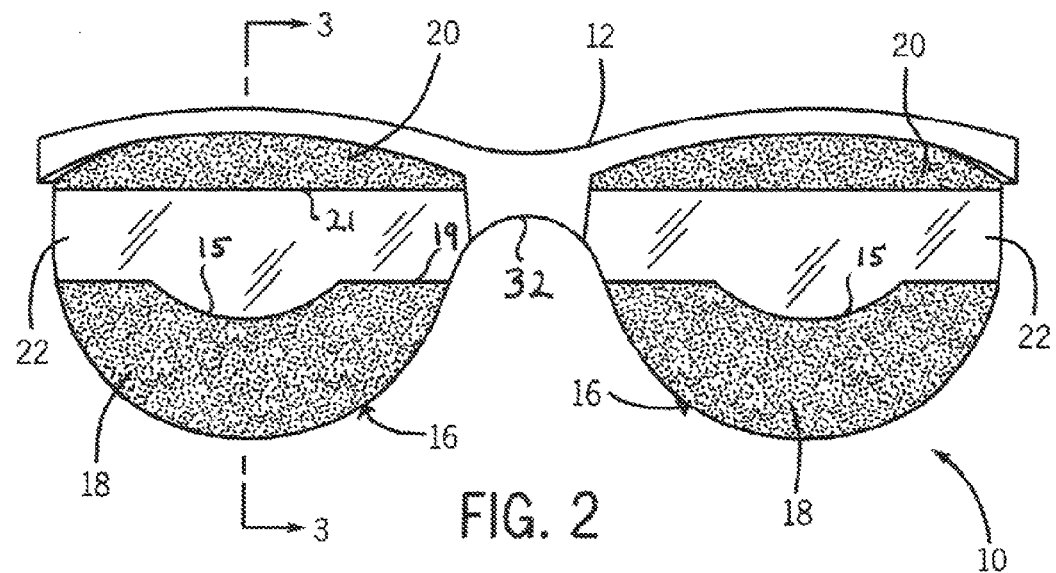
FIG. 2 is a front view of the athletics visual aid focus device of FIG. 1.

Referring to FIGS. 1-3 an exemplary embodiment of an athletics visual aid focus device 10 is shown. The athletics visual aid focus device 10 includes a frame 12, configured to mount in front of a user's eyes, with an opaque upper portion 20 disposed to cover an upper peripheral vision along a horizontal plane above the user's eyes and an opaque lower portion 18 disposed to cover a lower peripheral vision along a horizontal plane below the user's eyes. In one aspect, the upper and lower opaque regions 18 and 20 may block out light peripherally above and below the eyes.

In one exemplary embodiment, the athletics visual aid focus device may be eyewear, for example, modified glasses. The athletics visual aid focus device 10 may include one or more lenses 16, a bridge 32 holding the frame 12 onto a user's nose, and one or more temples 30 that may be tensioned to assist in holding the athletics visual aid focus device 10 onto the user's head. The lenses 16 may be hard plastic or glass lenses. In one exemplary embodiment, the opaque upper portion 20 and the opaque lower portion 18 may be a dark tint integrated into the lens material. In another exemplary embodiment, the opaque upper portion 20 and the opaque lower portion 18 may be darkened hard plastic or soft vinyl covers affixed to either a rear surface 27 or front surface 23 of the lenses 16. In another exemplary embodiment, the frame 12 may not include lenses and the opaque upper portion 20 and the opaque lower portion 18 may be baffles attached to the frame 12.

The opaque upper portion 20 and the opaque lower portion 18 may be disposed spaced from one another. The lens 16 may include a transparent region 22 juxtaposed between the opaque upper portion 20 and the opaque lower portion 18. The transparent region 22 may extend laterally between one side edge 22a of the lens to the opposite side edge 22b. In exemplary embodiments that do not include a lens 16, the transparent region 22 may be open air. The height of the transparent region 22 and the spacing between the opaque upper portion 20 and the opaque lower portion 18, may be approximately the height of the user' eye. For example, the opaque upper portion 20 may include a lower edge 21 positioned proximate to the top 20a of and above the user's eye. The opaque lower portion 18 may include an upper edge 19 that may be positioned proximate to and below the bottom 18a of the user's eye. While the transparent region 22 is shown with substantially parallel lower and upper edges 19 and 21, another exemplary embodiment may include lower and upper edges 19 and 21 that taper in narrowing fashion toward one another toward the outer edges of the lenses 16.

In one aspect, the athletics visual aid focus device 10 may accommodate varying eye sizes by including a depression 15 along the lower edge 19. The depression 15 may provide an eye mark for proper positioning of the eyes while using the athletics visual aid focus device 10. The depression 15 may also provide for an unobstructed field of vision just around the user's pupil in what is an otherwise obstructed view. Looking again to FIG. 2 the depression 15 has a chord 17 running from a depression inside corner 15a to a depression outside corner 15b, and the depression 15 further has a rise 15c between the chord 17 and the lowest point 15d in the depression 15. In another aspect, looking to FIG. 2, the opaque lower portion 18 has a bottom edge 19b and may be disposed to allow a batter to see through the lens 16 below the opaque lower portion 18 through a lower transparent region 22b.

Referring now to FIGS. 3 and 4, an exemplary use of the athletics visual aid focus device 10 is shown. A baseball player may wear the athletics visual aid focus device 10 during the act of batting to better focus on hitting the ball. The opaque upper portion 20 and the opaque lower portion 18 may limit the batter's field of view by blocking out light rays BL that are in horizontal planes above and below the user's eyes. The light rays UL and LL shown may represent boundaries of the horizontal planes above and below the user's eyes. Thus, the transparent region 22 may define a tunnel vision by allowing light rays between and including rays UL and LL under the lower edge 21 and above the upper edge 19 respectively to reach the user's eyes. Additionally, exemplary embodiments including the depression 15 that is shown in FIGS. 1-2 may allow more light rays DL shown in FIG. 3 through the transparent region exposed by the depression 15. Thus, distractions that may have otherwise been detectable in the light rays BL are blocked from the user's sight while the user may be allowed to focus on, for example, a pitched ball that is viewable within the athletics visual aid focus device 10 transparent region 22. Yet, other exemplary embodiments may include a lower transparent region 22b allowing light rays between and including bottom upper ray BUL and bottom lower ray BLL below the bottom edge 19b enabling the baseball player to position his feet without moving his head. The bottom edge 19b may be between 1 mm and 4 mm from the lowest point 19c of the lens 16.

While the foregoing has been described in the context of use by a baseball batter, it will be understood that other athlete's may benefit from the tunnel vision provided by the athletics visual aid focus device 10. For example, a basketball player may employ the athletics visual aid focus device 10 during shooting and a golfer may employ the device 10 during a golf swing.

It should be understood, of course, that the foregoing relates to exemplary embodiments of the invention and that modifications may be made without departing from the spirit and scope of the invention as set forth in the following claims.

What is claimed is:

1. A visual aid focus device, comprising:
   a frame;
   at least a lens coupled to the frame;
   an opaque upper portion of the lens;
   an opaque lower portion of the lens; and
   a transparent region juxtaposed between the opaque upper and lower portions of the lens; said opaque upper portion separate from said opaque lower portion; said opaque upper portion having a lower edge and said opaque lower portion having an upper edge; said upper and lower edges being adjacent to the transparent region; said transparent region extending laterally from a one side edge of the lens to an opposite side edge; the opaque lower portion disposed to provide for a lower transparent region below the opaque lower portion; further comprising a depression in the opaque lower portion of the lens, the depression formed on the upper edge of the opaque lower portion; and the depression disposed proximate in front of a user's pupil when the visual aid focus device is worn; and the opaque upper portion is an upper baffle and the opaque lower portion is a lower baffle.

2. The visual aid focus device of claim 1, wherein the lower edge of the opaque upper portion is positioned proximate to and above a user's eye.

3. The visual aid focus device of claim 2 wherein the upper edge of the opaque lower portion is positioned proximate to and below the user's eye.

4. The visual aid focus device of claim 3 wherein the opaque upper portion and the opaque lower portion are covers.

5. The visual aid focus device of claim 4 wherein the opaque upper portion and the opaque lower portion are configured to be mounted in front of a front surface of the lens and also to the rear of a rear surface of the lens.

6. The visual aid focus device of claim 1 wherein the opaque upper portion and the opaque lower portion are covers configured to be affixed to a front surface of the lens and also to a rear surface of the lens.

7. A visual aid focus device, comprising:
   a frame;
   at least a lens coupled to the frame;
   an opaque upper portion of the lens;
   an opaque lower portion of the lens;
   a transparent region juxtaposed between a lower edge of the opaque upper portion and an upper edge of the opaque lower portion; the transparent region running from a one side edge to an opposite side edge of the lens; the lower edge of the opaque upper portion positioned proximate to and above an user's eye; the opaque lower portion disposed to provide for a lower transparent region below the opaque lower portion; further comprising a depression in the opaque lower portion of the lens, the depression formed on the upper edge of the opaque lower portion; and the depression disposed proximate in front of a user's pupil when the visual aid focus device is worn; and the opaque upper portion being an upper baffle and the opaque lower portion is a lower baffle.

8. The visual aid focus device of claim 7 wherein the lower transparent region is through a bifocal area of the lens.

9. The visual aid focus device of claim 7, wherein the upper and the lower baffles are covers configured to be mounted in front of a front surface of the lens, and also configured to be mounted to a rear of a rear surface of the lens.

10. The visual aid focus device of claim 7, wherein the transparent region broadens as a user looks toward a user's ear.

11. The visual aid focus device of claim 7 wherein the transparent region tappers in a narrowing fashion as a user looks toward a user's ear.

12. A visual aid focus device, comprising:
a frame;
at least a lens coupled to the frame;
an opaque upper portion of the lens;
an opaque lower portion of the lens;
and a transparent region juxtaposed between the opaque upper and lower portions of the lens; said opaque upper portion separate from said opaque lower portion; said opaque upper portion having a lower edge and said opaque lower portion having an upper edge; said upper and lower edges being adjacent to the transparent region; said transparent region extending laterally from a one side edge of the lens to an opposite side edge; said transparent region generally a height of a user's eye; the height as measured from a top of the user's eye to a bottom of the user's eye when the user is standing erect and looking straight ahead; further comprising a depression in the opaque lower portion of the lens, the depression disposed in the upper edge and proximate in front of a user's pupil when the visual aid focus device is worn; and the opaque upper portion being an upper baffle and the opaque lower portion being a lower baffle.

13. The visual aid focus device of claim 12, wherein the opaque lower portion is disposed to provide for a lower transparent region below the baffle opaque lower portion.

14. The visual aid focus device of claim 13 wherein the opaque upper portion and the opaque lower portion are covers.

15. The visual aid focus device of claim 12 wherein the opaque lower portion is disposed to provide for a lower transparent region below the opaque lower portion.

16. The visual aid focus device of claim 15 wherein the opaque upper portion and the opaque lower portion are covers.

17. The visual aid focus device of claim 12 wherein the transparent region is tinted to reduce blue light.

* * * * *